(12) United States Patent
Wang

(10) Patent No.: US 10,582,853 B2
(45) Date of Patent: Mar. 10, 2020

(54) SELECTIVE ILLUMINATION FUNDUS IMAGING

(71) Applicant: Welch Allyn, Inc., Skaneateles Falls, NY (US)

(72) Inventor: Ynjiun Paul Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 129 days.

(21) Appl. No.: 15/919,955

(22) Filed: Mar. 13, 2018

(65) Prior Publication Data

US 2019/0282089 A1    Sep. 19, 2019

(51) Int. Cl.
*A61B 3/14*    (2006.01)
*A61B 3/00*    (2006.01)
*A61B 5/00*    (2006.01)
*A61B 3/12*    (2006.01)

(52) U.S. Cl.
CPC .............. *A61B 3/14* (2013.01); *A61B 3/0008* (2013.01); *A61B 3/0025* (2013.01); *A61B 3/12* (2013.01); *A61B 5/0013* (2013.01)

(58) Field of Classification Search
CPC ....... A61B 3/14; A61B 3/0008; A61B 3/0025; A61B 3/12; A61B 5/0013
See application file for complete search history.

(56) References Cited

U.S. PATENT DOCUMENTS

| | | | |
|---|---|---|---|
| 5,835,214 A | 11/1998 | Cabib et al. | |
| 5,861,939 A | 1/1999 | Heacock | |
| 5,992,744 A | 11/1999 | Smith et al. | |
| 6,142,629 A | 11/2000 | Adel et al. | |
| 6,198,532 B1 | 3/2001 | Cabib et al. | |
| 6,276,798 B1 | 8/2001 | Gil et al. | |
| 6,361,167 B1 | 3/2002 | Su et al. | |
| 6,952,498 B2 | 10/2005 | Ishikura | |
| 7,134,754 B2 | 11/2006 | Kerr et al. | |
| 7,677,730 B2 | 3/2010 | Shimizu | |
| 8,078,267 B2 | 12/2011 | Gellerman et al. | |
| 8,326,405 B2 | 12/2012 | Gellerman et al. | |
| 8,491,120 B2 | 7/2013 | Kahn et al. | |
| 8,807,751 B2 | 8/2014 | Kahn et al. | |
| 9,247,876 B2 | 2/2016 | Cornsweet et al. | |

(Continued)

FOREIGN PATENT DOCUMENTS

| | | |
|---|---|---|
| DE | 60204678 T2 | 5/2006 |
| JP | 2017-158828 A | 9/2001 |
| JP | 2014-073205 A | 4/2014 |

OTHER PUBLICATIONS https://www.designworldonline.com/an-algorithm-for-cmos-image-intensity-flicker-reduction/, An Algorithm for CMOS Image Intensity Flicker Reduction, accessed Feb. 5, 2018, 4pgs.

(Continued)

*Primary Examiner* — Wen Huang
(74) *Attorney, Agent, or Firm* — Merchant & Gould P.C.

(57) ABSTRACT

Fundus imaging includes selective illumination and exposure of an image sensor array. Fundus imaging systems and methods disclosed herein are wide field of view imaging typically conducted under non-mydriatic conditions. At a first time, an illumination unit illuminates a first portion of an eye fundus. At a second time, the illumination unit illuminates a second portion of the eye fundus. One or more fundus images are captured during illumination.

17 Claims, 8 Drawing Sheets

(56) References Cited

U.S. PATENT DOCUMENTS

| | | |
|---|---|---|
| 9,498,126 B2 | 11/2016 | Wang |
| 9,579,018 B2 | 2/2017 | Cornsweet et al. |
| 2006/0134004 A1 | 6/2006 | Gellermann et al. |
| 2006/0244913 A1 | 11/2006 | Gellermann et al. |
| 2009/0079936 A1 | 3/2009 | Robert |
| 2009/0153798 A1 | 6/2009 | Dick et al. |
| 2015/0098059 A1 | 4/2015 | Ou-Yang et al. |
| 2016/0166142 A1 | 6/2016 | Kobayashi |
| 2016/0213249 A1 | 7/2016 | Cornsweet et al. |
| 2017/0007119 A1 | 1/2017 | Cornsweet et al. |
| 2017/0035292 A1 | 2/2017 | Wang |
| 2017/0196452 A1 | 7/2017 | Wang |
| 2017/0224212 A1 | 8/2017 | Cornsweet et al. |

OTHER PUBLICATIONS https://www.azom.com/article.aspx?ArticieID=12647, Rolling Shutter vs. Global Shutter CCD and CMOS Image Sensors—The Differences Between and Advantages of Each Mode, accessed Feb. 14, 2018, 13pgs.

International Search Report and Written Opinion in PCT/US2019/021860 dated Jun. 20, 2019, 12 pages.

SELECTIVE ILLUMINATION FUNDUS IMAGING

INTRODUCTION

People with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Trained medical professionals use cameras during eye examinations for diabetic retinopathy screening. The cameras can produce images of the back of the eye and trained medical professionals use those images to diagnose and treat diabetic retinopathy.

These images are produced either with pharmacological pupil dilation, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments. Medical professionals can also use fundus imaging apparatus to detect or monitor other diseases, such as hypertension, glaucoma, and papilledema.

SUMMARY

Embodiments of the disclosure are directed to fundus imaging, typically under non-mydriatic conditions. Generally, systems and methods disclosed herein selectively illuminate portions of an eye fundus and coordinate these illuminations with image sensor array exposure. Various aspects are described in this disclosure, which include, but are not limited to, the following aspects.

In one aspect, a non-mydriatic fundus imaging system includes an illumination unit, a rolling shutter image sensor array (also referred to as a rolling reset image sensor array) including a plurality of rows of pixels, a processing unit, and memory. The memory encodes computer executable instructions that, when executed by the processing unit, cause the non-mydriatic fundus imaging system to: illuminate, with the illumination unit, a first area of a fundus; while the first area of the fundus is illuminated, expose a first portion of the plurality of rows of pixels; stop illuminating the first area of the fundus; illuminate, with the illumination unit, a second area of the fundus; and, while the second area of the fundus is illuminated, expose a second portion of the plurality of rows of pixels. In some instances, there is overlap between the first area and the second area.

In another aspect, a method of imaging a fundus under non-mydriatic conditions is disclosed. The method includes illuminating a first area of the fundus using an illumination unit; while illuminating the first area of the fundus, exposing a first portion of a plurality of rows of pixels of a global shutter image sensor array; stopping illuminating the first area of the fundus; illuminating a second area of the fundus using the illumination unit; and while illuminating the second area of the fundus, exposing a second portion of the plurality of rows of pixels of the global shutter image sensor array.

In another aspect, a method of imaging a fundus under non-mydriatic conditions is disclosed. The method includes illuminating a first area of the fundus using an illumination unit, while illuminating the first area of the fundus, exposing a first portion of a plurality of pixels of a rolling shutter image sensor array, stopping illuminating the first area of the fundus, illuminating a second area of the fundus using the illumination unit, and, while illuminating the second area of the fundus, exposing a second portion of the plurality of rows of pixels of the rolling shutter image sensor array. In some instances, there is overlap between the first area and the second area.

In another aspect, a non-mydriatic fundus imaging apparatus includes a first light-emitting diode (LED) array, a second LED array, an image sensor array including a plurality of rows of pixels, a processing unit, and memory. The memory stores instructions that, when executed by the processing unit, cause the non-mydriatic fundus imaging apparatus to: during a first time period, illuminate the first LED array; capture a first image by exposing, during the first time period, the plurality of rows of pixels in a first area as global shutter operation; during a second time period, illuminate the second LED array; and capture a second image by exposing, during the second time period, the plurality of rows of pixels in a second area as global shutter operation.

The details of one or more embodiments are set forth in the accompanying drawings and the description below. Other features, objects, and advantages of these embodiments will be apparent from the description, drawings, and claims.

DESCRIPTION OF THE FIGURES

The following drawing figures, which form a part of this application, are illustrative of described technology and are not meant to limit the scope of the disclosure in any manner.

DETAILED DESCRIPTION

Figure 1:
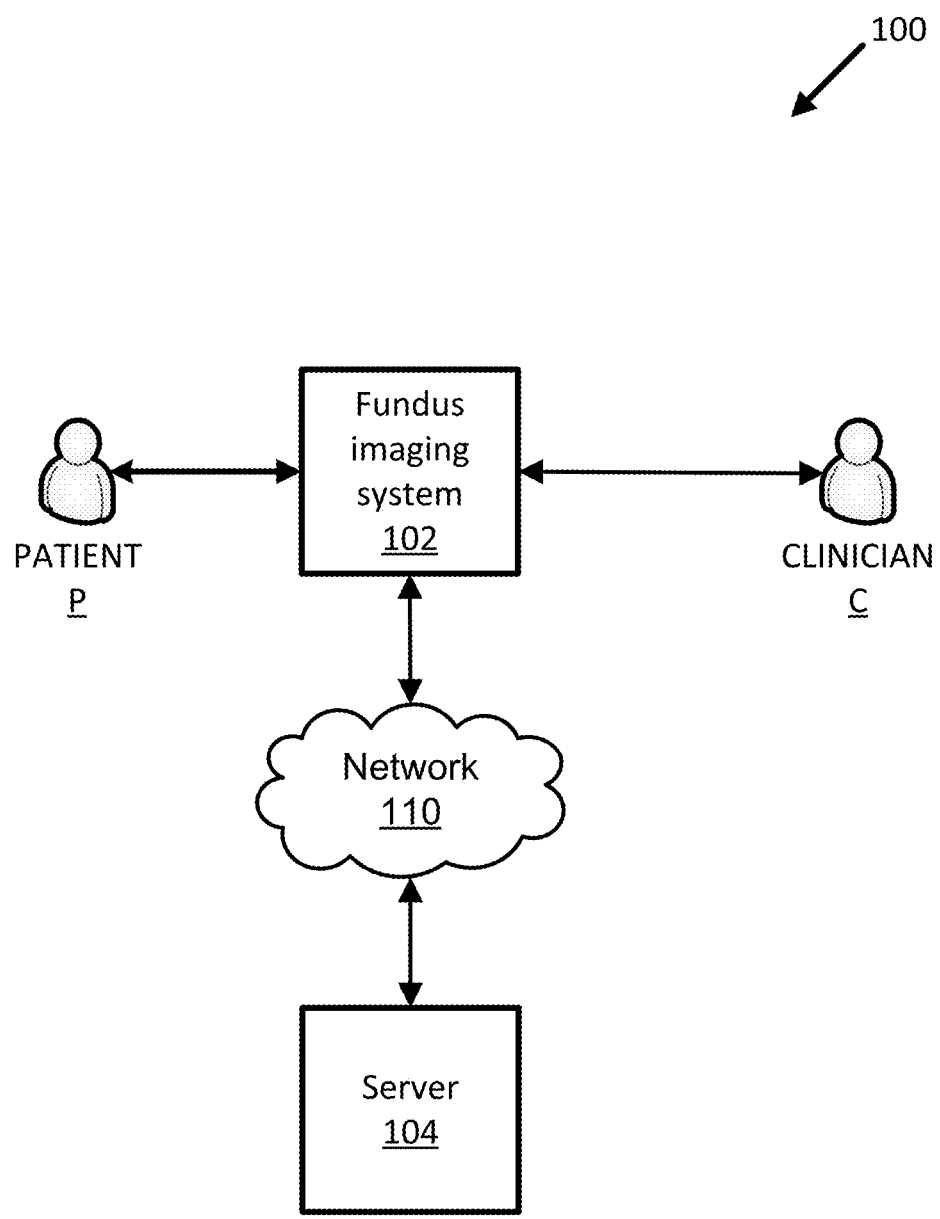
FIG. 1 is a schematic view of an example fundus imaging environment.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

Broadly, the present disclosure is directed to non-mydriatic fundus imaging. Typical fundus imaging disclosed herein uses digital cameras. In particular, systems and methods of this disclosure are directed towards wide field of view (FOV) fundus imaging.

Existing wide FOV fundus imaging systems can produce fundus images with undesirable artifacts. For example, traditional illumination systems utilized in wide FOV fundus imaging systems can produce images with bright spots caused by reflection of light from the cornea and/or blue glare caused by iris-cornea reflection(s). As a result, wide FOV fundus imaging systems can undesirably produce images with one or more bright spots. In some instances, the bright spots appear near the top middle and bottom middle of the image.

Systems and methods disclosed and contemplated herein coordinate illumination with image sensor array exposure to avoid or minimize the aforementioned bright spots in images. Systems and methods described below include multiple illumination sources. In some instances, illumination of the multiple illumination sources is coordinated with exposure of a rolling shutter image sensor array. In other instances, illumination of the multiple illumination sources is coordinated over multiple areas of exposures of an image sensor array configured for global shutter operations.

FIG. 1 shows example fundus imaging environment 100. Example fundus imaging environment 100 includes fundus imaging system 102 that is in communication with network 110 and server 104 in communication with network 110. Clinician C uses fundus imaging system 102 to obtain one or more fundus images of patient P. The example fundus imaging environment 100 is particularly well suited for non-mydriatic fundus imaging. Other embodiments can include more or fewer components.

Fundus imaging system 102 obtains one or more images of the eye fundus of patient P. As used herein, "fundus" refers to the eye fundus and includes the retina, optic nerve, macula, vitreous, choroid and posterior pole. In this example, one or more images of the eye are desired.

Fundus imaging system 102 can be used to assist clinician C in screening for, monitoring, or diagnosing various eye diseases, such as hypertension, diabetic retinopathy, glaucoma and papilledema. It will be appreciated that the clinician C that operates the fundus imaging system 102 can be different from the clinician C evaluating the resulting image(s). For instance, fundus imaging system 102 can be used to provide images of the eye to diagnose or monitor the progression of a disease such as diabetic retinopathy.

Fundus imaging system 102 is usually configured for wide field of view (FOV) imaging. Generally, wide FOV imaging means the system is capable of capturing images with a field of view angle greater than a particular threshold. Specific to fundus imaging, wide FOV can be defined by a number of fields included in a single image capture. The Early Treatment Diabetic Retinopathy Study (ETDRS) identifies various fields in fundus imaging. Traditional non-wide FOV fundus imaging systems usually require multiple images to capture more than one ETDRS field.

In contrast, fundus imaging system 102 can capture multiple ETDRS fields in a single image capture. For example, fundus imaging system 102 can capture a macula centered fundus image (ETDRS Field 1M) and an optic disc centered fundus image (ETDRS Field 2) in a single image capture. In some instances, fundus imaging system 102 has a 40 degree wide FOV. Optionally, fundus imaging system 102 has a 50 degree wide FOV. In some implementations, fundus imaging system 102 has a 55 degree wide FOV. In still other implementations, fundus imaging system 102 has a 60 degree wide FOV.

Wide FOV fundus cameras, by nature of the expanded field of view, and a subject to undesirably capturing reflections of illuminations in the images. Fundus imaging system 102 avoids capturing images with these eye fundus reflections by coordinating illumination of an illumination unit with image sensor array exposure.

One technique for fundus imaging requires mydriasis, dilation of a patient's pupil, which can be painful and/or inconvenient to the patient P. Example fundus imaging system 102 is configured for non-mydriatic conditions. That is, fundus imaging system 102 can capture wide FOV images without requiring a mydriatic drug to be administered to the patient P before imaging. In terms of pupil dilation, fundus imaging system 102 can capture wide FOV images with pupil sizes as small as 2.5 mm. In some instances, fundus imaging system 102 can capture wide FOV images with pupil sizes as small as 3.5 mm. Of course, fundus imaging system 102 can image the eye fundus if a mydriatic drug has been administered.

Fundus imaging system 102 includes a housing that supports system components. For instance, the housing supports one or two apertures for imaging one or two eyes at a time. In some embodiments, the housing supports positional guides for the patient P, such as an adjustable chin rest. The positional guides help align the patient's P eyes with the apertures. In some embodiments, the apertures are adjustable to align them with the patient's P eyes. Once the patient's P eyes are aligned, clinician C can initiate image capture sequencing.

Fundus imaging system 102 is typically connected to network 110. Network 110 can include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and an external display using one or more wired or wireless protocols, such as Bluetooth, Wi-Fi Direct, radio-frequency identification (RFID), or Zigbee. Other configurations are possible.

Server 104 communicates with fundus imaging system 102 and additional devices. For example, server 104 receives fundus images from fundus imaging system 102 and stores the images, and possible accompanying data such as patient data, in one or more databases. Clinicians can then access stored images for analysis. Server 104 includes one or more components of computing device 801 shown in FIG. 8, described in more detail below.

Figure 2:
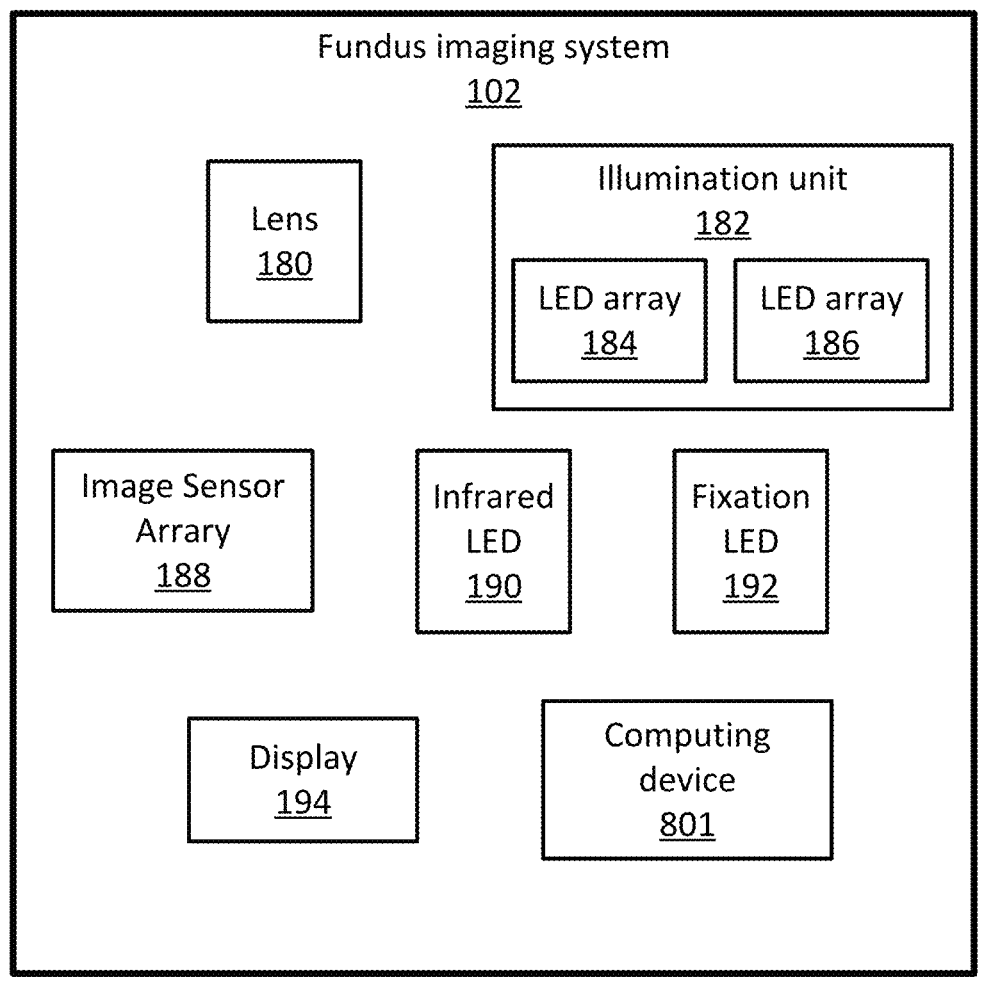
FIG. 2 is a schematic diagram showing example components of the fundus imaging system used in the environment of FIG. 1.

FIG. 2 is a schematic diagram showing example components of fundus imaging system 102. Fundus imaging system 102 includes lens 180, illumination unit 182, image sensor array 188, infrared LED 190, fixation LED 192, display 194, and computing device 801. Each component is in communication with, at least, computing device 801. Commercial embodiments of fundus imaging system 102 include the Welch Allyn RetinaVue™ 100 Imager and the Welch Allyn RetinaVue™ 700 Imager (Welch Allyn, Skaneateles Falls, N.Y.). Other embodiments can include more or fewer components.

Lens 180 focuses light onto image sensor array 188. Typically, lens 180 is adjustable. For example, lens 180 can be implemented as a variable focus liquid lens or a mechanically adjustable lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting. A mechanically adjustable lens can change a focal length of the lens using, for example, by a stepping motor, a voice coil, an ultrasonic motor, or a piezoelectric actuator.

Illumination unit 182 illuminates the eye fundus during image capture. Illumination unit 182 is configured to illuminate at least two different areas of the eye fundus. Typically, the different fundus areas are illuminated at different times. These illuminations are coordinated with operation of image sensor array 188.

As shown, illumination unit 182 includes LED array 184 and LED array 186. In other embodiments, illumination unit 182 can include one or more additional lighting units. In addition, lighting elements in illumination unit 182 can include non-light-emitting diode components. LED array 184 and LED array 186 can be single color or multi-color or white. For example, LED array 184 is a three-channel RGB LED, where each die is capable of independent and tandem operation. Typically, LED array 184 and LED array 186 emit light at a same wavelength that is in the visible spectrum.

LED array 184 and LED array 186 are arranged to illuminate different, but typically complementary, areas of the eye fundus. For example, LED array 184 is arranged to illuminate a bottom area of the eye fundus and LED array 186 is arranged to illuminate a top area of the eye fundus. As another example, LED array 184 is arranged to illuminate a left area of the eye fundus and LED array 186 is arranged to illuminate a right area of the eye fundus. Relative terminology used when discussing illumination, such as top, bottom, left, and right, generally refers to those portions from which reflections would result in bright spots in the top, bottom, left, or right of image sensor array 188.

Image sensor array 188 receives and processes light reflected by the patient's fundus. Image sensor array 188 can be a complementary metal-oxide semiconductor (CMOS) sensor array or a charge coupled device (CCD) sensor. Image sensor array 188 has a plurality of rows of pixels and a plurality of columns of pixels. For example, in various implementations, the image sensor array has about 1280 by 1024 pixels, about 640 by 480 pixels, about 1500 by 1152 pixels, about 2048 by 1536 pixels, or about 2560 by 1920 pixels. Other pixel sizes are possible.

Pixels in image sensor array 188 include photodiodes that have a light-receiving surface and have substantially uniform length and width. During exposure, the photodiodes convert the incident light to a charge. In various implementations, exposure and readout of image sensor array 188 can be performed as rolling shutter, global reset, or global shutter.

In rolling shutter exposure and readout, each row of pixels is exposed for the same time duration, however, each row of pixels is exposed at different points in time. Rolling shutter exposure begins at a top row of image sensor array 188 and each row below is successively exposed and then readout. Typically, exposure of the row below begins before completing exposure and readout of the row above. In this way, at any given time during image sensor array 188 exposure, more than one row of pixels are exposed.

In global reset, the photodiodes in the image sensor array 188 begin collecting charge simultaneously, unlike the row-by-row exposure used in rolling shutter operation. However, global reset is similar to rolling shutter operation in that each row is read out successively, typically from top to bottom of the image sensor array 188.

In global shutter operation, all of the photodiodes in a first area in image sensor array 188 are exposed simultaneously and for the same length of time. Then readout is performed for each photodiode. In some instances, while reading out the first area in image sensor array 188, fundus imaging system 102 will initiate a second illumination and expose a second area in image sensor array 188 simultaneously.

Global shutter operation shares some similarities with global reset operation, but there are also differences in operation and physical configuration of the image sensor arrays capable of such operations. The simultaneous exposure of pixels in global shutter operation is similar to global reset operation. However, global shutter operation differs from global reset operation in that global shutter operation stops exposure at the same time, rather than the row-by-row readout of global reset. Typically, a CMOS sensor supporting global shutter operation has 5 transistors in each pixel and requires shielding in each pixel, such as opaque metal shielding. In contrast, a CMOS sensor supporting rolling reset typically has 3 transistors in each pixel and does not have shielding in each pixel.

Infrared LED 190 illuminates the eye fundus with near-infrared light. Typically, infrared light emitted by infrared LED 190 is used during a preview mode. For example, clinician C can use a preview mode to determine or estimate the patient's P eye focus without illuminating visible light that could cause the pupil to contract or irritate the patient P.

Fundus imaging system 102 optionally includes fixation LED 192. Fixation LED 192 produces light to guide the patient's P eye for alignment. Fixation LED 192 can be a single color or multicolor LED. For example, the fixation LED 192 can produce a beam of green light that appears as a green dot when patient P looks into the fundus imaging system 102. Other colors and designs, such as a cross, "x" and circle are possible.

Fundus imaging system 102 can also include display 108. Display 108 shows fundus images captured by fundus imaging system 102. In the example embodiment, a housing supports display 108. In other embodiments, display 108 connects to the image processor through wired or wireless connection, and can be instantiated as a smart phone, tablet computer, or external monitor.

Fundus imaging system 102 also includes computing device 801, which typically includes a processing unit and a computer readable storage device. In some embodiments, the computer-readable storage device stores data instructions, which when executed by the processing device, causes the processing device to perform one or more of the functions, methods, or operations, described herein. An example computing device 801 is illustrated and discussed in more detail with reference to FIG. 8.

Figure 3:
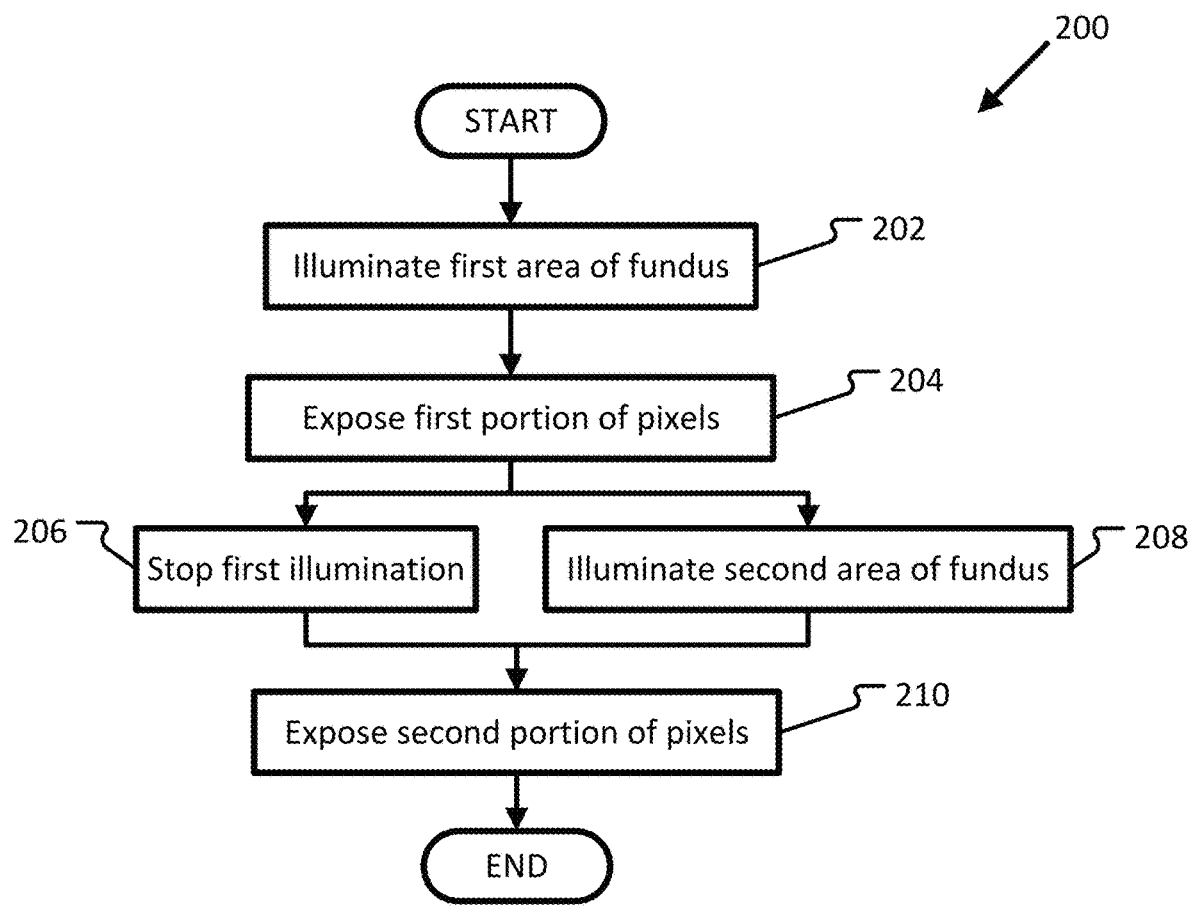
FIG. 3 illustrates an example method of imaging an eye fundus.

FIG. 3 illustrates example method 200 for imaging an eye fundus. Example method 200 includes illuminating a first area of the fundus (operation 202), exposing a first portion of pixels (operation 204), stopping the first illumination (operation 206), illuminating a second area of the fundus (operation 208) and exposing a second portion of pixels (operation 210). Example method 200 is usually performed without administering mydriatic substances to the patient. That is, method 200 is conducted under non-mydriatic conditions where, in some instances, the patient's pupil dilation can be as small as 2.5 mm. Other embodiments can include more or fewer operations.

Figure 4:
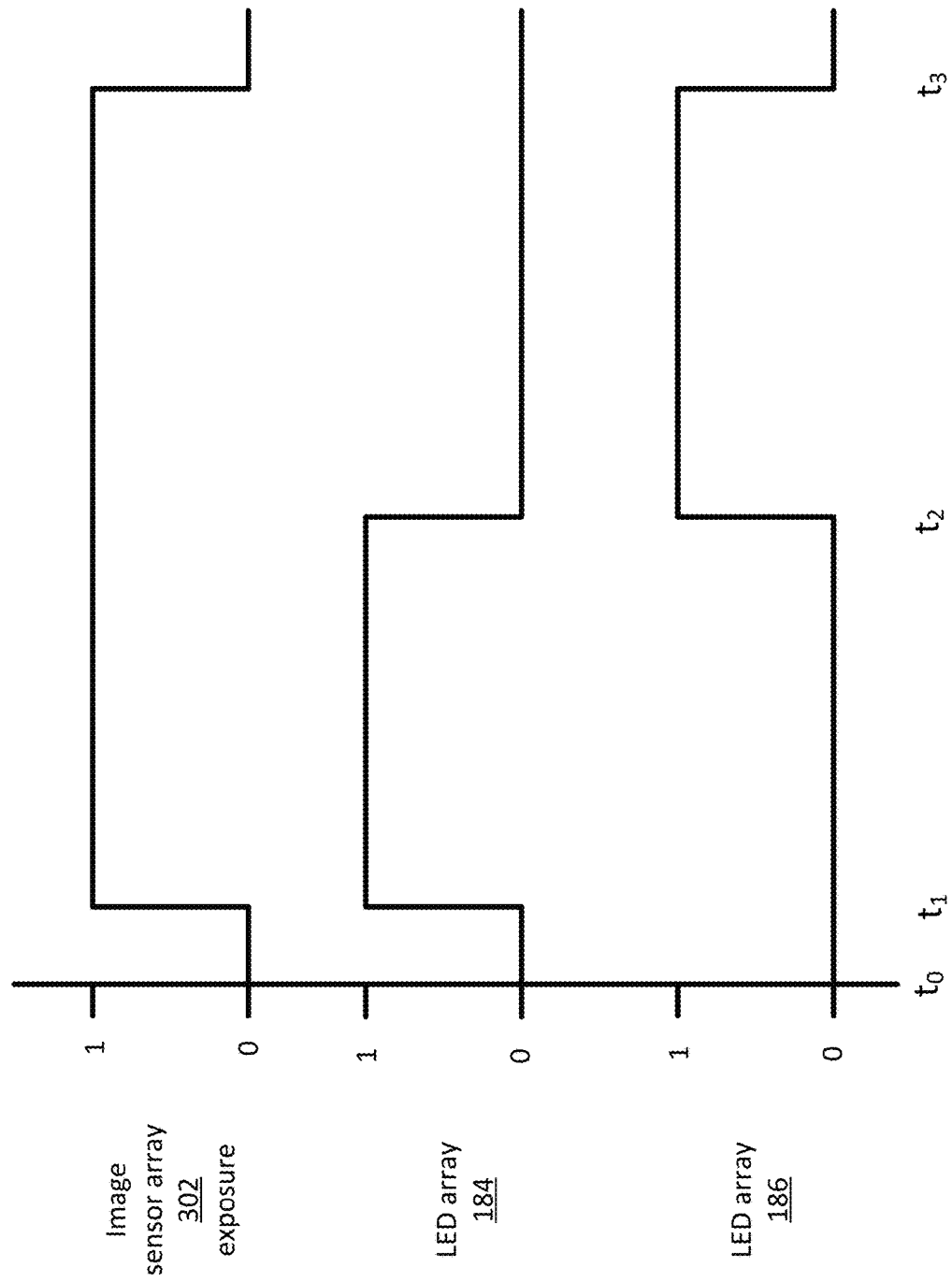
FIG. 4 shows a schematic timing diagram for certain components of the fundus imaging system of FIG. 2 performing the method of FIG. 3.
Figure 5A:
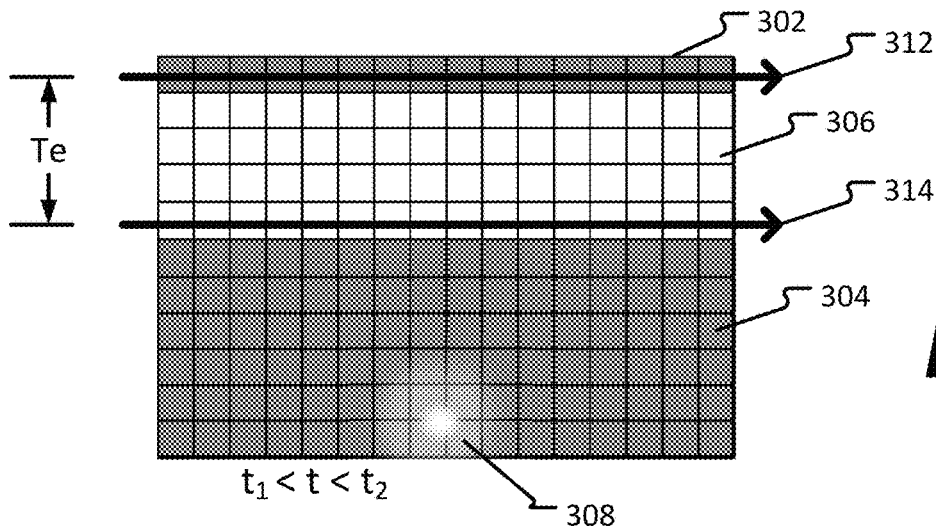
FIGS. 5A-5C schematically illustrate operation of an image sensor array at various points during the method of FIG. 3.
Figure 5B:
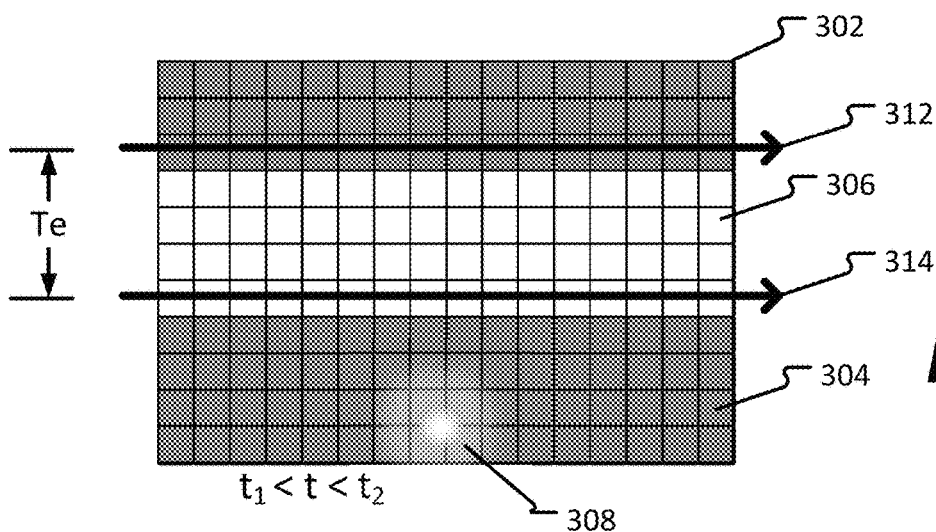
Figure 5C:
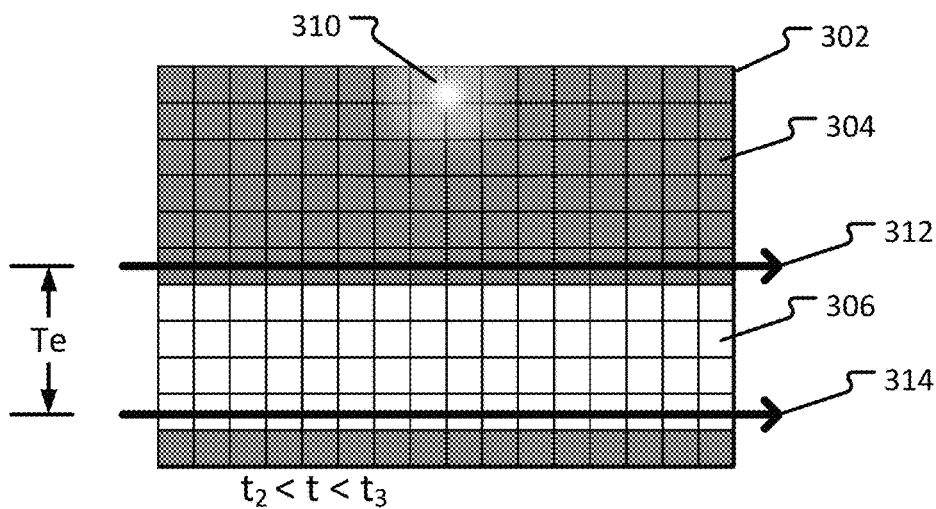

FIG. 4, discussed concurrently below, shows a schematic timing diagram for certain components of a fundus imaging system performing example method 200. More particularly, FIG. 4 shows timing for operation of image sensory array 302 exposure, LED array 184, and LED array 186. FIGS. 5A-5C, discussed concurrently below, schematically illustrate operation of image sensor array 302 at various points during example method 200.

Example method 200 utilizes rolling reset operation of an image sensor array. In combination, an illumination unit configured to illuminate at least a portion of the first area of the fundus and at least a portion of a second area of the fundus is also employed. It will be appreciated that example method 200 can be modified appropriately if more than two light sources are utilized.

Example method 200 begins with a start operation, which is typically initiated by a clinician using an interface provided by the fundus imaging system. Additionally, one or more preview or pupil tracking operations can be performed prior to execution of operations shown in example method 200. These precursor operations can, for example, determine that the pupils of the patient are properly aligned with an imaging axis of the fundus imaging system.

Illuminating a first area of the fundus (operation 202) includes causing a portion of a first area of fundus to be illuminated with an illumination unit. The portion of the fundus illuminated (called fundus reflection) is related to the exposed pixels being exposed. More specifically, an illumination area is preferably where light reflected from the cornea does not reflect onto a pixel that is being exposed. So, for example, when rolling reset exposure begins at a top row of an image sensor array, the first area of the funds illuminated will be a portion of the eye cornea from which reflected light (called cornea reflection) is not incident on the top row(s) of the image sensor array. In other words, example method 200 enables the image sensor array to only be exposed to fundus reflection and avoid exposing that portion of the image sensor array to cornea reflection at the same time.

Typically, at the same time as the first area illumination (operation 202) or shortly thereafter, a first portion of pixels are exposed (operation 204) in the image sensor array. In some implementations, the first portion of pixels includes the top row of pixels to the halfway point of pixels. In other implementations, the first portion of exposed pixels can include slightly more than half or slightly less than half of the total rows of pixels in the image sensor array.

An example implementation for a 5 megapixel image sensor array is as follows. A 5MP image sensor array includes 2560 by 1944 pixels (columns by rows). So the first portion of pixels includes the first row of pixels through the $872^{nd}$ row of pixels. Accordingly, a second portion of pixels includes the $873^{rd}$ row of pixels through the $1944^{th}$ row of pixels.

Referring to FIG. 4, time $t_0$ corresponds to a time prior to exposure and/or illumination of LED array 184. At time $t_1$, a signal is sent to image sensor array 302 to begin exposure of the pixels as a rolling shutter operation. This is shown in FIG. 4 as a signal going from zero to 1. Also at time $t_1$, a signal is sent to LED array 186, part of the illumination unit, to begin illumination of a first area of the fundus.

FIG. 5A shows, schematically, image sensor array 302 at a time period between $t_1$ and $t_2$, most precisely just after time $t_1$. FIG. 5A schematically shows image sensor array 302, not exposed pixels 304, exposed pixels 306, light reflection 308 from LED array 184, readout 312, and reset 314. For purposes of discussion, FIGS. 5A-5C show image sensor array 302 as having 12 rows of pixels. In actual implementation, image sensor array 302 would have many more pixels. As an example, a 5 megapixel image sensor array would have dimensions of 2560×1944, that is, 2560 columns and 1944 rows of pixels.

As shown in FIG. 5A, the top row of image sensor array 302 has been reset, exposed and is undergoing readout 312. Pixels in the three rows below that top row are at various stages of exposure. Additionally, the fifth row from the top row is undergoing reset operations 314. A time between pixel reset and readout is shown in FIGS. 5A-5C as exposure time $T_e$.

During the pixel exposure shown in FIG. 5A, LED array 184 illuminates a first area of the eye fundus. Reflection from the eye cornea onto image sensor array 302 is shown schematically as light 308. Broadly speaking, the fundus imaging system is arranged such that light 308 is at an opposite end of image sensor array 302 from where pixel readout 312 and pixel reset 314 are occurring. In this way, light from LED array 184 is not incident on exposed pixels and does not appear in a resulting image. As shown, LED array 184 is oriented such that light 308 is near a bottom center portion of image sensor array 302. Other positions of light 308 are possible, for instance, a right, bottom portion or a left, bottom portion of image sensor array 302.

Referring to FIG. 5B, readout 312 and reset 314 have progressed to a later time than that shown in FIG. 5A, but still before time $t_2$ (shown in FIG. 4). Thus, LED array 184 is still illuminating the first area of the eye fundus in the schematic snapshot shown in FIG. 5B.

Referring again to FIG. 3, after exposure of the first portion of pixels (operation 204), illumination of the first area is stopped (operation 206). This is shown in FIG. 4 as time $t_2$. At time $t_2$, LED array 184 receives a signal to cease illumination.

A second area of the fundus is illuminated (operation 208), at time $t_2$, when the first illumination is ceased (operation 206). The second area of the fundus is typically at an opposite end of the eye fundus. In some instances, there can be some overlap in the illuminated first area of the fundus and the illuminated second area of the fundus.

In other implementations, operation 208 can occur slightly before or slightly after operation 206. Illuminating a second area of the fundus (operation 208) with LED array 186 is shown in FIG. 4 at time $t_2$. As shown in FIG. 4, from time to until time $t_2$, LED array 186 was not illuminated. But at time $t_2$, LED array 186 receives a signal and is illuminated.

Exposure of a second portion of pixels (operation 210) generally occurs beginning at time $t_2$ until time $t_3$. As shown in FIG. 4, image sensor array 302 does not necessarily receive a different input during exposure of a second portion of pixels (operation 210) from the input initiating exposure of the first portion of pixels (operation 204). Rather, exposing the second portion of pixels (operation 210) is a continuation of the exposure. That is, exposing the second portion of pixels (operation 210) is included in example method 200 to illustrate that the rolling reset exposure has progressed to where illumination of the second area of the fundus (operation 208) will not result in a reflection onto the currently-exposed portion of pixels.

FIG. 5C shows readout 312 and reset 314 as well as light 310 at some time between $t_2$ and $t_3$ as depicted in FIG. 4. Light 310, schematically shown in FIG. 5C, is a reflection of light from a patient eye cornea onto image sensor array 302. As shown in FIG. 5C, light 310 is generally near a top central portion of image sensor array 302, which is opposite the portion of the image sensor array where pixels are being exposed.

After each row in image sensor array 302 has been reset and readout, time $t_3$ in FIG. 4, exposure of the image sensor array 302 ceases, illumination of LED array 186 ceases, and example method 200 ends.

Figure 6:
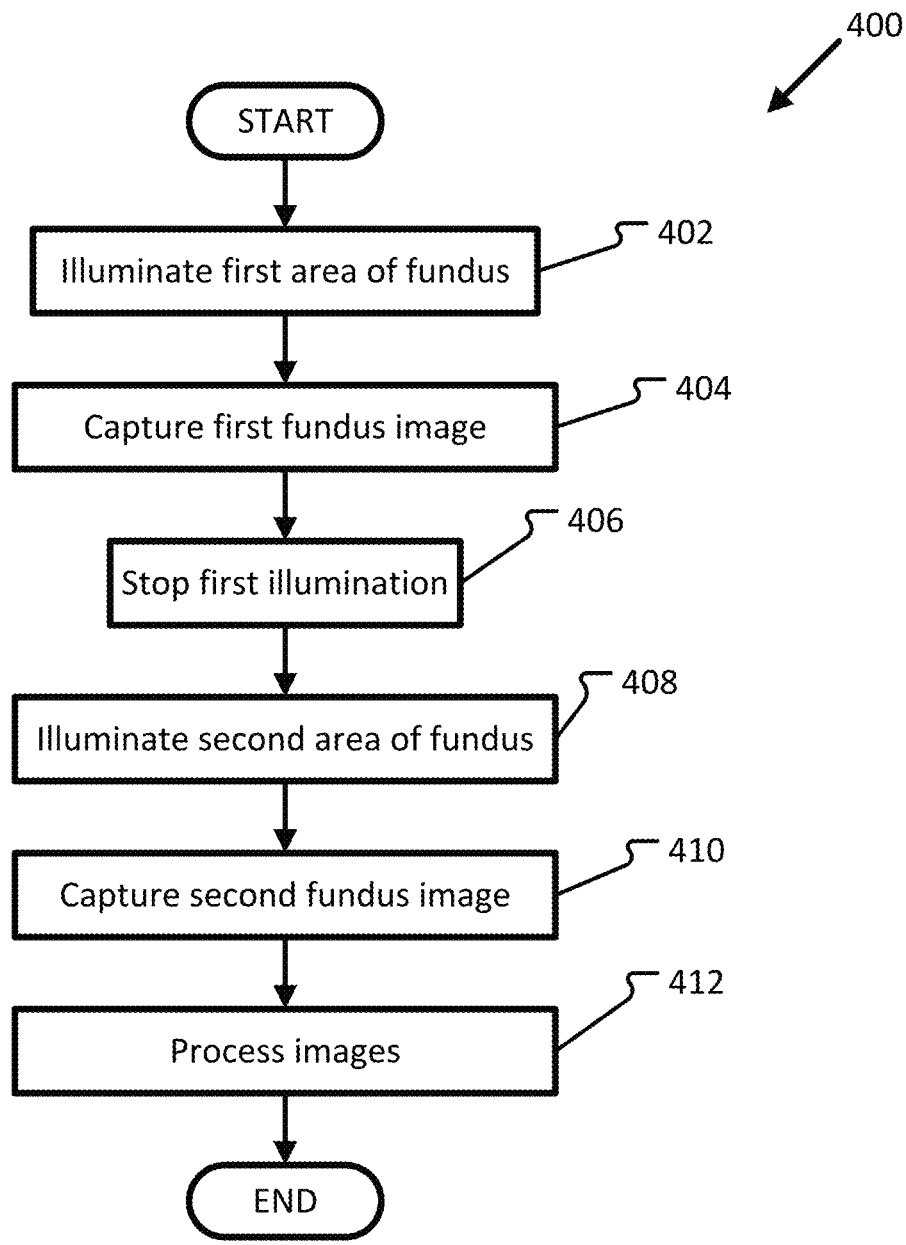
FIG. 6 illustrates another example method of imaging an eye fundus.

FIG. 6 shows example method 400 for imaging an eye fundus. Example method 400 includes illuminating a first area of a fundus (operation 402), capturing a first fundus image (operation 404), stopping the first illumination (operation 406), illuminating a second area of a fundus (operation 408), capturing a second fundus image (operation 410), and processing images (operation 412). Example method 400 is usually performed without administering mydriatic substances to the patient. That is, method 400 is conducted under non-mydriatic conditions. Other embodiments can include more or fewer operations.

Example method 400 utilizes global shutter operation of an image sensor array. To broadly contrast example methods 200 and 400, example method 400 typically includes illuminating a first portion of the image sensor array during a first image capture, and then illuminating an opposite portion of the image sensor array during a second image capture. This is in contrast to the illumination of the top area and bottom area of the image sensor array during a single image capture as in example method 200. Additionally, illumination during example method 400 can result in reflections onto the left side portion and/or right side portion of the image sensor array. In some instances, method 400 can be performed using an image sensor array that is configured for rolling reset.

Example method 400 begins with a start operation, which is typically initiated by a clinician using an interface provided by the fundus imaging system. Additionally, one or more preview or pupil tracking operations can be performed prior to execution of operations shown in example method 400. These precursor operations can, for example, determine that the pupils of the patient are properly aligned with an imaging axis of the fundus imaging system.

After the start operation, a first area of a fundus is illuminated (operation 402). Typically, the first area of the fundus is an area that results in a reflection from the fundus onto the sensor array in a left side portion or right side portion of the image sensor array. Illuminating the first area of the fundus (operation 402) is complimentary to illuminating the second area of the fundus (operation 408), such that between the two illumination areas, all or a majority of the eye fundus area that is imaged is illuminated between the two images captured.

During illumination of the first area of the fundus (operation 402), a first fundus image is captured (operation 404). Capturing the first fundus image (operation 404) is performed with global shutter operation. As discussed above, global shutter operation involves simultaneous exposure and then simultaneous readout of the photodiodes in the image shutter array. After capturing the first fundus image (operation 404), illumination of the first area is ceased (operation 406).

Next, a second area of the fundus is illuminated (operation 408). If the first area of the fundus resulted in light incident on a left center portion of the image sensor array, then the second area of the fundus illuminated would result in a reflection of light onto the right center portion of the image sensor array. During this second illumination (operation 408), a second fundus image is captured (operation 410). Capturing the second fundus image (operation 410) is also performed as global shutter operation. Illumination of the second area of the fundus ceases after capturing the second fundus image.

After capturing the first and second fundus images, those images undergo image processing (operation 412) to generate a composite image. Image processing includes combining the two images such that any portions of the images including flash artifacts are removed and replaced with the non-flash artifact portion from the complimentary image in the final, resulting image. In this way, although the first image and the second image include fundus reflections, a resulting image combining the two images does not include those reflections.

Figure 7:
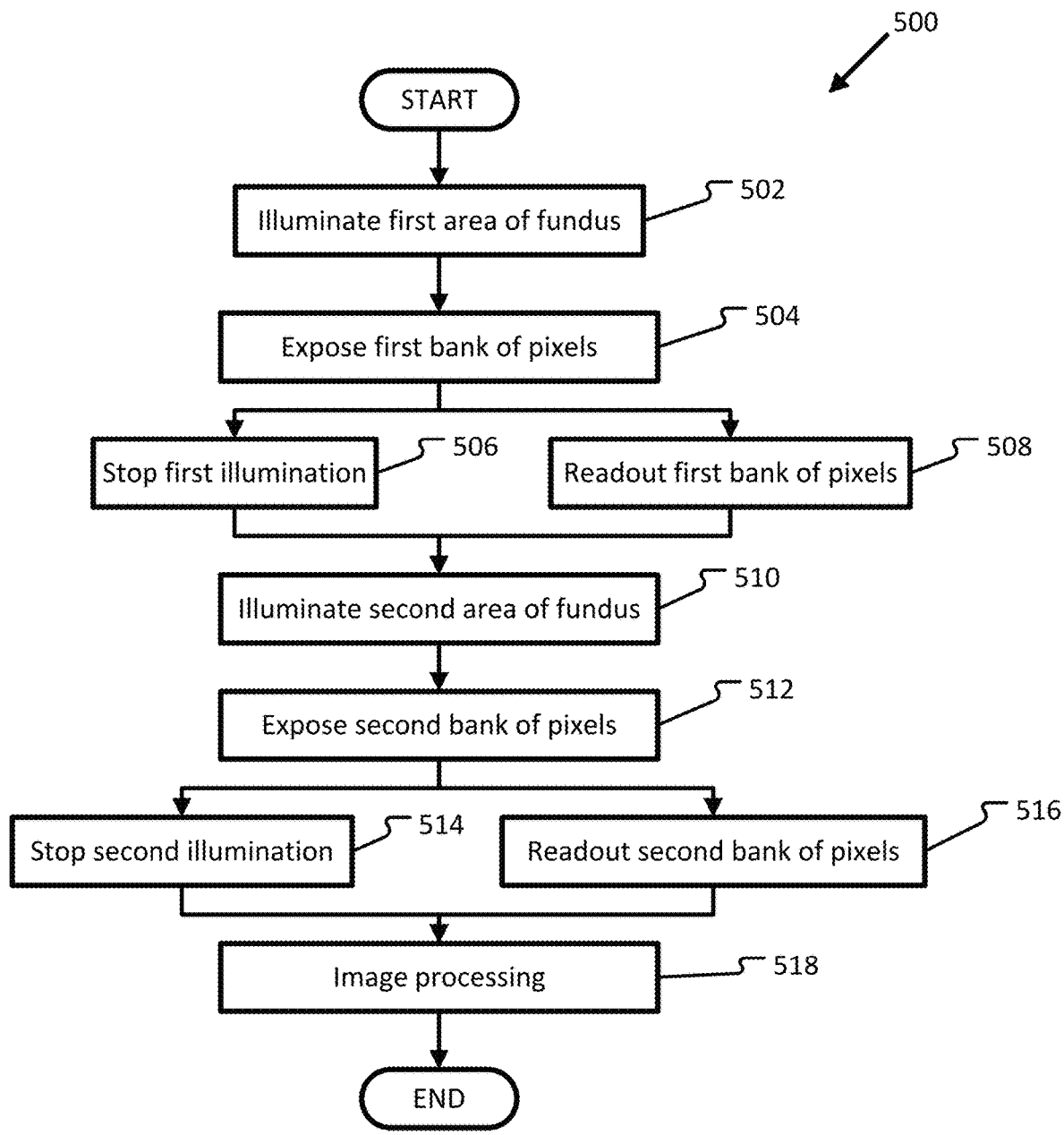
FIG. 7 illustrates another example method of imaging an eye fundus.

FIG. 7 shows example method 500 for imaging an eye fundus. Example method 500 includes illuminating a first area of a fundus (operation 502), exposing a first bank of pixels (operation 504), stopping the first illumination (operation 506), reading out the first bank of pixels (operation 508), illuminating a second area of the fundus (operation 510), exposing a second bank of pixels (operation 512), stopping the second illumination (operation 514), reading out the second bank of pixels (operation 516), and processing images (operation 518). Other embodiments can include more or fewer operations.

Broadly, method 500 involves selective, top and bottom illuminations combined with selective global shutter operation of the image sensor array. Method 500 begins by illuminating a first area of a subject's fundus (operation 502), similar to operation 202 described above. During illumination of the first area (operation 502), a first bank of pixels in the image sensor array are exposed (operation 504) as global shutter.

Typically, exposing the first bank of pixels (operation 504) includes exposing a top half of the image sensor array. For example, in an image sensor array having 1944 rows, row 1 through row 872 are simultaneously exposed during operation 504. Then illumination of the first area is stopped (operation 506). In parallel, the first bank of pixels are read out (operation 508).

Next, a second area of the fundus is illuminated (operation 510). Illuminating the second area (operation 510) is similar to operation 208 described above. At the same time, a second bank of pixels of the image sensor array are exposed (operation 512).

Typically, exposing the second bank of pixels (operation 512) includes exposing a bottom half of the image sensor array. In the example image sensor array above having 1944 rows, operation 512 includes exposing row 873 through row 1944 simultaneously.

After illuminating the second area (operation 510) and exposing the second bank of pixels (operation 512), the illumination of the second area is stopped (operation 514). In parallel, the second bank of pixels are read out (operation 516). Then the image is processed (operation 518).

Figure 8:
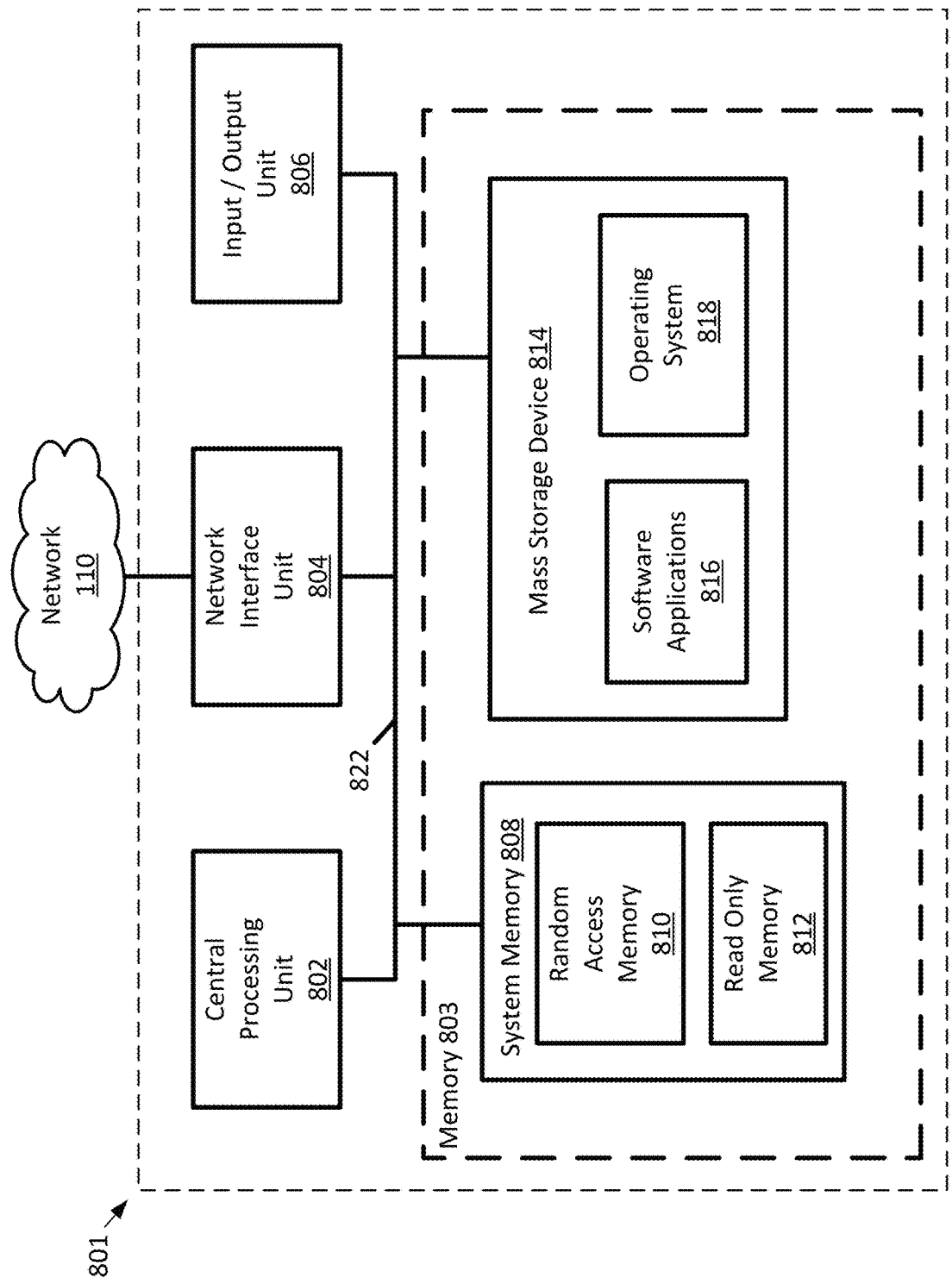
FIG. 8 shows example physical components of a computing device of the fundus imaging system shown in FIG. 2.

FIG. 8 shows an example computing device 801 of fundus imaging system 102. As illustrated, example computing device 801 includes at least one central processing unit ("CPU") 802, memory 803, and a system bus 822 that couples memory 803 to the CPU 802. Memory 803 includes system memory 808 and mass storage device 814. System memory 808 includes a random access memory ("RAM") 810 and a read-only memory ("ROM") 812. A basic input/output system that contains the basic routines that help to transfer information between elements within the example computing device 801, such as during startup, is stored in the ROM 812. Memory 803 further includes mass storage device 814. Mass storage device 814 is able to store software applications 816, operating system 818, and data.

Mass storage device 814 is connected to CPU 802 through a mass storage controller (not shown) connected to the system bus 822. Mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central processing unit can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this disclosure. For example, the mass storage device 814 and/or the RAM 810 can store software instructions that, when executed by the CPU 802, cause the fundus imaging system 102 to capture fundus images.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A non-mydriatic fundus imaging system, comprising:
   an illumination unit;
   a rolling reset image sensor array, including a plurality of rows of pixels;
   a processing unit; and
   memory encoding computer executable instructions that, when executed by the processing unit, cause the non-mydriatic fundus imaging system to:
   illuminate, with the illumination unit, a first area of a fundus, the first area including one of at least a bottom area of the fundus or at least a top area of the fundus;
   while the first area of the fundus is illuminated, expose a first portion of the plurality of rows of pixels;
   stop illuminating the first area of the fundus;
   illuminate, with the illumination unit, a second area of the fundus, the second area including an other of the bottom area of the fundus or the top area of the fundus, and the bottom area not overlapping the top area; and
   while the second area of the fundus is illuminated, expose a second portion of the plurality of rows of pixels.

2. The non-mydriatic fundus imaging system according to claim 1, wherein the rolling reset image sensor array is a complementary metal oxide semiconductor (CMOS) image sensor array configured for a rolling shutter exposure, with:
   the first portion of the plurality of rows of pixels being exposed as the rolling shutter exposure; and
   the second portion of the plurality of rows of pixels being exposed as the rolling shutter exposure.

3. The non-mydriatic fundus imaging system according to claim 1, the illumination unit including a first light source and a second light source.

4. The non-mydriatic fundus imaging system according to claim 3, the first light source being arranged to at least partially illuminate the first area of the fundus; and
   the second light source being arranged to at least partially illuminate the second area of the fundus.

5. The non-mydriatic fundus imaging system according to claim 3, the first light source being a first light emitting diode array; and
   the second light source being a second light emitting diode array.

6. The non-mydriatic fundus imaging system according to claim 5, a wavelength of the first light emitting diode array being equal to a wavelength of the second light emitting diode array.

7. The non-mydriatic fundus imaging system according to claim 1, the plurality of rows of pixels having a top portion and a bottom portion; and
   the first portion of the plurality of rows of pixels being exposed starting at the top portion of the plurality of rows of pixels.

8. The non-mydriatic fundus imaging system according to claim 7, the second portion of the plurality of rows of pixels being exposed continuing at a top of the bottom portion of the plurality of rows of pixels.

9. The non-mydriatic fundus imaging system according to claim 1, the second area overlapping at least a portion of the first area.

10. A method of imaging a fundus under non-mydriatic conditions, the method comprising:
    illuminating a first area of the fundus using an illumination unit, the first area including one of at least a bottom area of the fundus or at least a top area of the fundus;
    while illuminating the first area of the fundus, exposing a first portion of a plurality of rows of pixels of a global shutter image sensor array;
    stopping illuminating the first area of the fundus;
    illuminating a second area of the fundus using the illumination unit, the second area including an other of the bottom area of the fundus or the top area of the fundus, and the bottom area not overlapping the top area; and
    while illuminating the second area of the fundus, exposing a second portion of the plurality of rows of pixels of the global shutter image sensor array.

11. The method according to claim 10, wherein exposing the first portion of the plurality of rows of pixels includes exposing the plurality of rows of pixels as a global shutter exposure; and
    wherein exposing the second portion of the plurality of rows of pixels includes exposing the plurality of rows of pixels as the global shutter exposure.

12. The method according to claim 11, wherein illuminating the first area of the fundus includes illuminating a first light source of the illumination unit; and
    wherein illuminating the second area of the fundus includes illuminating a second light source of the illumination unit.

13. The method according to claim 11, further comprising reading out the first portion of the plurality of rows of pixels as global shutter readout, wherein reading out the first portion of the plurality of rows of pixels occurs in parallel with stopping illuminating the first area of the fundus.

14. The method according to claim 13, further comprising:
    reading out the second portion of the plurality of rows of pixels as global shutter readout; and
    stopping illuminating the second area of the fundus, wherein reading out the second portion of the plurality of rows of pixels occurs in parallel with stopping illuminating the second area of the fundus.

15. A non-mydriatic fundus imaging apparatus, comprising:
    a first light-emitting diode (LED) array;
    a second LED array;
    an image sensor array including a plurality of rows of pixels, the image sensor array configured for global shutter operation;
    a processing unit; and
    memory storing instructions that, when executed by the processing unit, cause the non-mydriatic fundus imaging apparatus to:
        during a first time period, illuminate the first LED array, the first LED array being configured to illuminate a first area of an eye fundus, the first area including one of at least a bottom area of the fundus or at least a top area of the fundus;
        capture a first image by exposing, during the first time period, the plurality of rows of pixels as global shutter operation;
        during a second time period, illuminate the second LED array, second LED array being configured to illuminate a second area of the eye fundus, the second area including an other of the bottom area of the fundus or the top area of the fundus, and the bottom area not overlapping the top area; and
        capture a second image by exposing, during the second time period, the plurality of rows of pixels as global shutter operation.

16. The non-mydriatic fundus imaging apparatus according to claim 15, the memory further storing instructions that, when executed by the processing unit, cause the non-mydriatic fundus imaging apparatus to generate a composite image by processing the first image and the second image.

17. The non-mydriatic fundus imaging apparatus according to claim 15, with the first area further including a left side portion of the eye fundus and the second area further including a right side portion of the eye fundus.

* * * * *